(12) United States Patent
Tanaka

(10) Patent No.: US 9,539,138 B2
(45) Date of Patent: Jan. 10, 2017

(54) METHOD OF OPHTHALMIC SURGERY AND KIT THEREFOR

(75) Inventor: Takao Tanaka, Tokyo (JP)

(73) Assignees: Takaya Tanaka, Tokyo (JP); SEIKAGAKU CORPORATION, Tokyo (JP); SANTEN PHARMACEUTICAL CO., LTD., Osaka (JP)

(*) Notice: Subject to any disclaimer, the term of this patent is extended or adjusted under 35 U.S.C. 154(b) by 1276 days.

(21) Appl. No.: 12/362,249

(22) Filed: Jan. 29, 2009

(65) Prior Publication Data

US 2009/0198213 A1 Aug. 6, 2009

Related U.S. Application Data

(60) Provisional application No. 61/024,589, filed on Jan. 30, 2008.

(51) Int. Cl.
| | |
|---|---|
| A61K 31/728 | (2006.01) |
| A61F 9/008 | (2006.01) |
| A61F 9/00 | (2006.01) |
| A61K 9/00 | (2006.01) |
| A61F 9/007 | (2006.01) |
| A61K 47/36 | (2006.01) |

(52) U.S. Cl.
CPC ........... *A61F 9/0017* (2013.01); *A61F 9/0008* (2013.01); *A61K 9/0048* (2013.01); *A61K 31/728* (2013.01); *A61F 9/007* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 4,141,973 A * | 2/1979 | Balazs | 514/54 |
| 5,273,056 A * | 12/1993 | McLaughlin et al. | 128/898 |
| 2002/0183279 A1 | 12/2002 | Tanaka | |
| 2004/0038936 A1 | 2/2004 | Tanaka | |
| 2004/0167480 A1 * | 8/2004 | Bos | 604/289 |
| 2004/0241155 A1 | 12/2004 | Shah | |

OTHER PUBLICATIONS

Matsubara et al., "Three Step Soft Shell Technique Using Dispersive-Cohesive Viscoelastic Materials," Japanese Journal of Ophthalmic Surgery 18 (3): 417-420 (2005).*
Ribeiro et al., "Effect of Concentration and Temperature on Surface Tension of Sodium Hyaluronate Saline Solutions," Langmuir 2007, 23, 7014-7017.*
Matsubara et al. ,Three Step Soft Shell Technique Using Dispersive-Cohesive Viscoelastic Materials, Japanese Journal of Ophthalmic Surgery 18 (3): 417-420, 2005.*
Steve A. Arshinoff, "Dispersive-cohesive viscoelastic soft shell technique," J Cataract Refract Surg, 1999, 25: 167-173.
Steve A. Arshinoff, "Using BSS with viscoadaptives in the ultimate soft-shell technique", J Cataract Refract Surg, 2002, 28: 1509-1514.
Hyojin Kim et al., "Efficacy of the soft-shell technique using Viscoat and Hyal-2000," J Cataract Refract Surg, 2004, 30: 2366-2370.
Ryuzi Yachimori et al, "Increased Intraocular Pressure and Corneal Endothelial Cell Loss Following Phacoemulsification Surgery", Opthalmic Surgery Lasers & Imaging, 2004, 35(6): 453-459.

* cited by examiner

*Primary Examiner* — Jeffrey S Lundgren
*Assistant Examiner* — Meghan Finn
(74) *Attorney, Agent, or Firm* — Sughrue Mion, PLLC

(57) ABSTRACT

A method of micro-incision ophthalmic surgery, comprising, in the order mentioned, the steps of:
(1) injecting a first viscoelastic substance through an incision site which is lateral to corneal into an anterior chamber which is in an opposite part of the incision site with discharging aqueous humor;
(2) injecting a second viscoelastic substance having higher surface tension than that of the first viscoelastic substance through the incision site into the remaining anterior chamber unfilled with the first viscoelastic substance; and
(3) injecting a third viscoelastic substance having lower surface tension than that of the second viscoelastic substance through the incision site into an area of the anterior chamber which is filled with the first viscoelastic substance until the incision site is sealed with the already injected the second viscoelastic substance.

12 Claims, 2 Drawing Sheets

METHOD OF OPHTHALMIC SURGERY AND KIT THEREFOR

BACKGROUND OF THE INVENTION

1. Field of the Invention

The present invention relates to a method of ophthalmic surgery and a kit therefor.

2. Brief Description of the Background Art

Various viscoelastic substances are used for supporting operations of micro-incision ophthalmic surgery in order to treat cataract and the like (patent literature1). In a known method of surgery, two different kinds of viscoelastic substances are used (patent literature 1 and non-patent literature 1).

The method in which two kinds of viscoelastic substances are used is called the soft shell technique. The method comprises placing in the position to contact with corneal endothelium a dispersion type viscoelastic substance, which shows high protective effects for corneal endothelium, and subsequently placing in the position capable of making the dispersion type viscoelastic substance tight on corneal endothelium a polymer coagulation type viscoelastic substance, which is effective in keeping cavity in an anterior chamber, as well as keeping cavity in the anterior chamber. As a result, a superior operation performance and protective effects for corneal endothelium can be achieved.

The soft shell technique is good since it has a superior operability and good protective effects for corneal endothelium, but it requires skills and gives different results depending on the skilled ophthalmologists. Furthermore, in cases where the soft shell technique is applied to glaucoma surgery, there are problems that intraocular pressure after surgery increases and the viscoelastic substance is difficult to be eliminated completely. If the viscoelastic substance cannot be eliminated completely, it may give a hotbed of postoperative bacterial endophthalmitis. Accordingly, the soft shell technique is not suitable for glaucoma surgery and the above-mentioned merits of the soft shell technique are not achieved on glaucoma surgery.

Therefore it is desired a method of ophthalmic surgery by which all ophthalmologists involved in an ophthalmic surgery can assure the uniformly quality and stable operative procedures and which can be used for glaucoma surgery and the like without anxiety.

Patent Document 1: U.S. Pat. No. 5,273,056

Non-Patent Document: Japanese Journal of Ophthalmic Surgery, Japanese Ophthalmological Society, 2005, July, vol. 18, No. 3, p. 417-420, published on Jul. 30, 2005

SUMMARY OF THE INVENTION

An object of the present invention is to provide a method of ophthalmic surgery which can successfully provide uniformly quality; as well as easy and stable operative procedures by ophthalmologists without considering their skill level with ophthalmic surgery and which can be used for various ophthalmic cases, and a kit therefor.

DETAILED DESCRIPTION OF THE INVENTION

Figure 1:
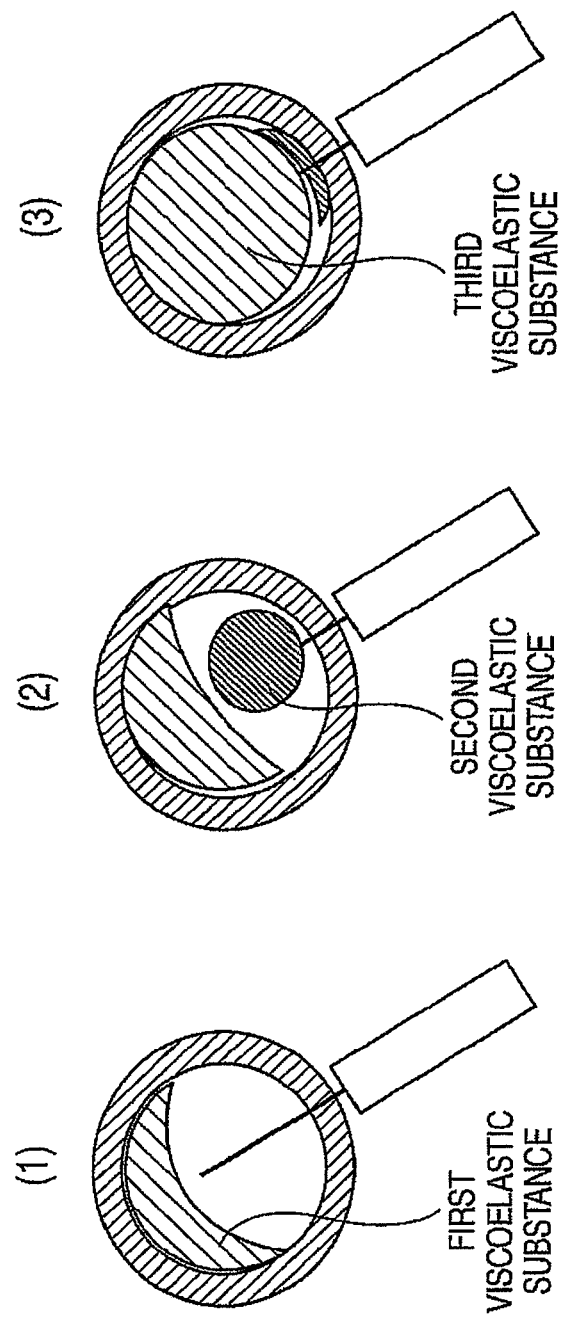
FIG. 1 is a schematic figure of the present invention method 1.

The inventors of the present invention intensively studied to achieve the above-mentioned object, and found that to inject respectively two viscoelastic substances which have different surface tensions into specific areas of an anterior chamber in a specific order can provide good operation performance and protective effects for corneal endothelium and can be operated with ease, stability and constant good quality by ophthalmologists without depending on their skill and experience level with ophthalmic surgery. As a result, they have provided a novel method of ophthalmic surgery. The method is called "Dual Visco Sealed-Up Technique".

Additionally, the inventors of the present invention further provide ophthalmic surgery support kits for Dual Visco Sealed-Up Technique.

The present invention provides a method of micro-incision ophthalmic surgery, which comprises, in the order mentioned, at least the steps of:

(1) injecting a first viscoelastic substance through an incision site which is lateral to cornea into an anterior chamber which is in an opposite part of the incision site with discharging aqueous humor;

(2) injecting a second viscoelastic substance having higher surface tension than that of the first viscoelastic substance through the incision site into the remaining anterior chamber unfilled with the first substance; and (3) injecting a third viscoelastic substance having lower surface tension than that of the second viscoelastic substance through the incision site into an area of the anterior chamber which is filled with the first viscoelastic substance until the incision site is sealed with the already injected the second viscoelastic substance, and the method is hereinafter referred to present invention method 1.

Preferable viscoelastic substances are aqueous solution containing a sugar chain. Preferable sugar chain is glycosaminoglycans. Preferable glycosaminoglycan is hyaluronic acid or a salt thereof.

A weight-average molecular weight of the hyaluronic acid or a salt thereof is preferably in the range of from 600,000 to 4,000,000.

Additionally, in the present invention method 1, the first viscoelastic substance in the above-mentioned step (1) and the third viscoelastic substance in the above-mentioned step (3) are preferably the same viscoelastic substance.

Furthermore, the first viscoelastic substance is preferably aqueous solution containing hyaluronic acid or a salt thereof, in which hyaluronic acid or a salt thereof has a weight-average molecular weight in the range of from 600,000 to 1,200,000. The second viscoelastic substance is preferably aqueous solution containing hyaluronic acid or a salt thereof, in which hyaluronic acid or a salt thereof has a weight-average molecular weight in the range of from 1,500,000 to 4,000,000, more preferably in the range of from 1,900,000 to 3,900,000.

Moreover, in cases where a viscoelastic substance is an aqueous solution containing hyaluronic acid or a salt thereof, a concentration of hyaluronic acid or a salt thereof in the aqueous solution is preferably about 1% (w/v).

Also the present invention further provides a method of micro-incision ophthalmic surgery, which comprises at least, in the order mentioned, the steps of:

(1) discharging an aqueous humor by anterior chamber paracentesis (2) injecting a second viscoelastic substance into an area around a puncture wound in an anterior chamber through the puncture wound; and
(3) injecting a first viscoelastic substance having a lower surface tension than that of the second viscoelastic substance into an area of the anterior chamber which is distant from an area which has already been filled with the second viscoelastic substance through the puncture wound until the puncture wound is sealed with the already injected second viscoelastic substance, (hereinafter referred to as the present invention method 2, and the present invention method 1 and the present invention method 2 are all together referred to hereinafter as the present invention method.)

The viscoelastic substances are preferably aqueous solution containing sugar chains. The sugar chain is preferably glycosaminoglycans. The glycosaminoglycan is preferably hyaluronic acid or a salt thereof.

A weight-average molecular weight of the hyaluronic acid or the salt thereof is preferably in the range of from 600,000 to 4,000,000.

Preferable first viscoelastic substance is aqueous solution containing hyaluronic acid or a salt thereof, in which hyaluronic acid or a salt thereof has a weight-average molecular weight in the range of from 600,000 to 1,200,000. Preferable second viscoelastic substance is aqueous solution containing hyaluronic acid or a salt thereof, in which hyaluronic acid or a salt thereof has a weight-average molecular weight in the range of from 1,500,000 to 4,000,000, more preferably in the range of from 1,900,000 to 3,900,000.

In cases where a viscoelastic substance is an aqueous solution containing hyaluronic acid or a salt thereof, a concentration of hyaluronic acid or a salt thereof in the aqueous solution is preferably about 1% (w/v).

Furthermore, the present invention further provides an ophthalmic surgery support kit for the present invention method. The kit comprises at least the following (A) and (B) as components;
(A) a first viscoelastic substance, and
(B) a second viscoelastic substance having a higher surface tension than that of the first viscoelastic substance.

Preferable viscoelastic substances are aqueous solution containing a sugar chain. Preferable sugar chain is glycosaminoglycans. Preferable glycosaminoglycan is hyaluronic acid or a salt thereof.

Preferable weight-average molecular weight of the hyaluronic acid or the salt thereof is in the range of from 600,000 to 4,000,000.

Preferable first viscoelastic substance is aqueous solution containing hyaluronic acid or a salt thereof, in which hyaluronic acid or a salt thereof has a weight-average molecular weight in the range of from 600,000 to 1,200,000. Preferable second viscoelastic substances is aqueous solution containing hyaluronic acid or a salt thereof, in which hyaluronic acid or a salt thereof has a weight-average molecular weight in the range of from 1,500,000 to 4,000,000, more preferably in the range of from 1,900,000 to 3,900,000.

In cases where a viscoelastic substance is an aqueous solution containing hyaluronic acid or a salt thereof, a concentration of hyaluronic acid or a salt thereof in the aqueous solution is preferably about 1% (w/v).

<1> The Present Invention Method 1

The present invention method 1 is a micro-incision ophthalmic surgery method which comprises, in order mentioned, at least the steps of:

(1) injecting a first viscoelastic substance through an incision site which is lateral to cornea into an anterior chamber which is in an opposite part of the incision site with discharging aqueous humor,
(2) injecting a second viscoelastic substance having higher surface tension than that of the first viscoelastic substance through the incision site into the remaining anterior chamber unfilled with the first viscoelastic substance; and
(3) injecting a third viscoelastic substance having lower surface tension than that of the second viscoelastic substance through the incision site into an area of the anterior chamber which is filled with the first viscoelastic substance until the incision site is sealed with the already injected the second viscoelastic substance.

<1>-1 a Viscoelastic Substance

A viscoelastic substance used for the present invention method 1 is not particularly limited as long as it is transparent viscoelastic substances which can be accepted medically and pharmaceutically.

Examples of the viscoelastic substances include aqueous solution containing sugar chains. In this case, needless to say, the term of "aqueous solution" includes physiological saline and the like.

Examples of the sugar chains used herein include, but not limited thereto, transparent viscoelastic substances of which solutions are acceptable in ophthalmic treatments. Examples of the sugar chains include glycosaminoglycans. Examples of the glycosaminoglycans include hyaluronic acid, chondroitin sulfate, chondroitin, dermatan sulfate, heparin, heparan sulfate and keratan sulfate, and salts thereof. Specifically it is preferable to use the above-mentioned sugar chains purified in high purity without including substantially contaminants which are not permitted to be contained in a drug.

Preferable examples of the viscoelastic substances used for the present invention method 1 include aqueous solution containing hyaluronic acid or a salt thereof and aqueous solutions containing both hyaluronic acid or a salt thereof and chondroitin sulfate or a salt thereof.

In this connection, the term of "salt" is not particularly limited as long as it is a medically and pharmaceutically acceptable salt. Examples of the salts include inorganic base salts such as alkaline metal salts (sodium salts, lithium salts, potassium salts and the like), alkaline earth metal salts and an ammonium salt and organic base salts such as diethanolamine salts, cyclohexylamine salts and amino acid salts. Among these, alkaline metal salts are preferable and a sodium salt is more preferable.

In cases where hyaluronic acid or a salt thereof is used herein, its weight-average molecular weight is preferably in the range of from 600,000 to 4,000,000.

The viscoelastic substances are commercially available as an ophthalmic surgical aid and such commercially available products may be used by itself on the present invention method 1. Examples of such commercial products include OPEGAN® (commercially available from SANTEN PHARMACEUTICAL CO., LTD. and manufactured by SEIKAGAKU CORPORATION.), OPEGAN Hi® (commercially available from SANTEN PHARMACEUTICAL CO., LTD. and manufactured by SEIKAGAKU CORPORATION), Healon® (commercially available from Advanced Medical Optics (AMO)), VISCOAT® (commercially available from Alcon), PROVISC® (commercially available from Alcon), OPELEAD® (commercially available from SENJU CORPORATION and manufactured by SHISEIDO) and the like. All of OPEGAN®, OPEGAN Hi® and PROVISC® are an aqueous solution of sodium hyaluronate and VISCOAT® is a composition of sodium hyaluronate and sodium chondroitin sulfate.

The first viscoelastic substance used in the step (1) of the present invention method 1 has a lower surface tension than that of a second viscoelastic substance used in the step (2). In other words, the second viscoelastic substance used in the step (2) of the present invention method 1 has a higher surface tension than that of the first viscoelastic substance used in the step (1).

The third viscoelastic substance used in the step (3) of the present invention method 1 has a lower surface tension than that of the second viscoelastic substance. The third viscoelastic substance is not particularly limited as long as it is a viscoelastic substance having a lower surface tension than that of the second viscoelastic substance in the step (2). The third viscoelastic substance may be either the same as or the different from the first viscoelastic substance used in the step (1). In cases where a viscoelastic substance used in the step (3) is the same as a first viscoelastic substance used in the step (1), it is enough that only two appropriate viscoelastic substances to each of the first viscoelastic substance and the second viscoelastic substance are prepared.

As described above, it is only necessary that the surface tension of each viscoelastic substance used in the present invention method 1 has the relation of "the first viscoelastic substance"<"the second viscoelastic substance" and "the second viscoelastic substance" >"the third viscoelastic substance". Therefore, it is also acceptable that "the first viscoelastic substance" and "the third viscoelastic substance" are the same in this invention method. Namely, in order to measure or determine a surface tension of viscoelastic substances used in the present invention method 1, the known methods can be used as long as the comparative relationship of surface tension can be determined.

In the present invention method 1, it is preferable that the first viscoelastic substance in the step (1) and the third viscoelastic substance in the step (3) are the same from the point of view of efficiency of surgical procedures and cost.

Specific preferable examples of the first viscoelastic substance include aqueous solution containing hyaluronic acid or a salt thereof, in which hyaluronic acid or a salt thereof has a weight-average molecular weight in the range of from 600,000 to 1,200,000. Specific preferable examples of the second viscoelastic substance include aqueous solution containing hyaluronic acid, in which hyaluronic acid or a salt thereof has a weight-average molecular weight in the range of from 1,500,000 to 4,000,000, more preferably in the range of from 1,900,000 to 3,900,000.

Accordingly, in cases where a first viscoelasic substance used in step (1) and the third viscoelastic substance used in step (3) are the same, the first viscoelastic substance in step (1) preferably is an aqueous solution containing hyaluronic acid or a salt thereof, in which hyaluronic acid or a salt thereof has a weight-average molecular weight in the range of from 600,000 to 1,200,000; preferable second viscoelastic substance in step (2) is an aqueous solution containing hyaluronic acid or a salt thereof, in which hyaluronic acid or a salt thereof has a weight-average molecular weight in the range of from 1,500,000 to 4,000,000 (more preferably 1,900,000 to 3,900,000), and preferable third viscoelastic substance having a lower surface tension than that of the second viscoelastic substance is an aqueous solution containing hyaluronic acid or a salt thereof, in which hyaluronic acid or a salt thereof has a weight-average molecular weight in the range of from 600,000 to 1,200,000.

Moreover in cases where a viscoelastic substance is an aqueous solution containing hyaluronic acid or a salt thereof, a concentration of hyaluronic acid or a salt thereof in the aqueous solution is preferably about 1% (w/v), specifically more preferably is 1% (w/v).

Accordingly, in cases where the first viscoelastic substance in the step (1) and the third viscoelastic substance in the step (3) are the same, it is preferable that the first viscoelastic substance in the step (1) is an aqueous solution containing hyaluronic acid or a salt thereof at a concentration of about 1% (w/v), in which hyaluronic acid or a salt thereof has a weight-average molecular weight in the range of from 600,000 to 1,200,000; the second viscoelastic substance in the step (2) is an aqueous solution containing hyaluronic acid or a salt thereof at a concentration of about 1% (w/v), in which hyaluronic acid or a salt thereof has a weight-average molecular weight in the range of from 1,500,000 to 4,000,000 (more preferably 1,900,000 to 3,900,000), and the third viscoelastic substance in the step (3) is an aqueous solution containing hyaluronic acid or a salt thereof at a concentration of about 1% (w/v), in which hyaluronic acid or a salt thereof has a weight-average molecular weight in the range of from 600,000 to 1,200,000. As mentioned above, it is preferable that all of the concentrations are 1% (w/v).

In cases where these viscoelastic substances are a commercially available product, it is preferable that the first viscoelastic substance in the step (1) and the third viscoelastic substance in the step (3) are the above-mentioned OPEGAN® and the second viscoelastic substance in the step (2) is the above-mentioned OPEGAN-Hi®. Note that OPEGAN® is a phosphate-buffered saline containing sodium hyaluronate having a weight-average molecular weight in the range of from 600,000 to 1,200,000 at a concentration of 1% (w/v) and OPEGAN Hi® is a phosphate-buffered saline containing sodium hyaluronate having a weight-average molecular weight in the range of from 1,900,000 to 3,900,000 at a concentration of 1% (w/v).

<1>-2 Specific Steps of the Present Invention Method 1

Feature of the present invention method 1 is a method of micro-incision ophthalmic surgery, which comprises, in the order mentioned, at least the following three steps of:

(1) injecting a first viscoelastic substance through an incision site which is lateral to cornea into an anterior chamber which is in an opposite part of the incision site with discharging aqueous humor;

(2) injecting a second viscoelastic substance having higher surface tension than that of the first viscoelastic substance through the incision site into the remaining anterior chamber unfilled with the first viscoelastic substance; and (3) injecting a third viscoelastic substance having a lower surface tension than that of said second viscoelastic substance through the incision site into an area of the anterior chamber which is filled with the first viscoelastic substance until the incision site is sealed with the already injected the second viscoelastic substance.

The step (1) is the step of injecting the first viscoelastic substance into an opposite part of an anterior chamber from an incision site which is lateral to cornea through the incision site with discharging aqueous humor.

The first viscoelastic substance used herein is as previously described. In the step (1), the first viscoelastic substance is injected into an anterior chamber through an incision site which is lateral to cornea in a micro-incision ophthalmic surgery. An area into which the first viscoelastic substance is injected is an opposite area from the incision site in the anterior chamber (i.e. the distant side from the incision site in the anterior chamber). Accordingly, it is one of the ways of the step (1) that a tip of device such as injector needle is placed in an appropriate position in order to inject the first viscoelastic substance into the opposite area from the incision site in the anterior chamber (i.e. the distant side from the incision in the anterior chamber), followed by injection of the first viscoelastic substance.

Volume of the first viscoelastic substance which is injected may be determined appropriately by those skilled in the art depending on a size of anterior chamber and a desired result of surgical on individual patients and the like. In cases where it is a cataract surgery on adult, if a shape of cornea which is viewed from directly above is "circle", for example, a volume of the first viscoelastic substance may be volume which can be filled up to approximately 50-60% of an area of the circle. Absolutely, the volume is not limited thereto.

As the first viscoelastic substance is injected gradually, in response to the injected volume, aqueous humor in the anterior chamber is discharged gradually through the incision site which is in lateral to cornea. The expression of "inject the viscoelastic substance with discharging aqueous humor" means such a situation mentioned above.

The step (2) which is carried out following the step (1) is the step of injecting a second viscoelastic substance having higher surface tension than that of the above-mentioned first viscoelastic substance into the remaining anterior chamber unfilled with the first viscoelastic substance.

The second viscoelastic substance used herein is as previously described. In the step (2), the second viscoelastic substance is injected into the anterior chamber through the incision site. An area in which the second viscoelastic substance is injected is a remaining anterior chamber unfilled with the first viscoelastic substance. In the step (1) the opposite area from the incision site in the anterior chamber (i.e. the area is at the distant side from the incision in the anterior chamber) is filled with the first viscoelastic substance. Accordingly, an area where the second viscoelastic substance should be injected in the step (2) is at the same side as the incision site in the anterior chamber. Therefore, it is one of the ways in the step (2) that a tip of device such as an injector needle which is used for injecting the viscoelastic substance is placed in an appropriate position which is capable that the second viscoelastic substance can be injected into the remaining anterior chamber unfilled with the first viscoelastic substance followed by injection of the second viscoelastic substance.

Volume of the second viscoelastic substance which is injected may be only enough volume to seal the incision site by treating in the step (3). Accordingly, in general, it is much less than a volume of the first viscoelastic substance injected in the step (1). An actual volume may be determined appropriately by those skilled in the art depending on a size of incision, a size of anterior chamber and a desired result of surgical on individual patients, and the like. In cases where it is a cataract surgery on adult, if a shape of cornea which is viewed from directly above is "circle", a volume which can be filled up to approximately 10 to 20% of an area of the circle may be represented as an example. Absolutely it is not limited thereto.

Also when a second viscoelastic substance is injected, aqueous humor in an anterior chamber may be discharged through an incision lateral to cornea depending on the injected volume of the second viscoelastic substance.

The step (3), which is performed following the step (2), is the step of injecting a third viscoelastic substance having a lower surface tension than that of the second viscoelastic substance through the incision site into the area filled with the first viscoelastic substance in the anterior chamber until the incision is sealed with the previously injected second viscoelastic substance.

The third viscoelastic substance used herein is as previously described. In the step (3), this viscoelastic substance is injected into the anterior chamber through the incision site. An area in which the viscoelastic substance should be injected is the area already filled with the first viscoelastic substance in the anterior chamber.

In the step (3), the third viscoelastic substance may be injected into the same area as the first viscoelastic substance is already injected into, which is in the opposite area from the incision site in the anterior chamber (i.e. the area is at a distant side from the incision site in the anterior chamber).

Accordingly, a tip of a device such an injector needle used for injecting the viscoelastic substance is placed in the appropriate position in order to inject the viscoelastic substance into the area filled with the first viscoelastic substance in the anterior chamber followed by injection of the viscoelastic substance.

Volume of the viscoelastic substance injected herein is volume which is enough to seal the incision site with the previously injected second viscoelastic substance. Therefore, actual volume depends on the amount of the previously injected first viscoelastic substance, the amount of the previously injected second viscoelastic substance, a size of the incision, a size of anterior chamber of each patient and the like.

In the step (3), aqueous humor is discharged through the incision site according to injecting a viscoelastic substance. Additionally, the previously injected second viscoelastic substance shifts toward the incision site in the flow of aqueous humor. Therefore, the step (3) can be achieved by injecting the third viscoelastic substance into the area of anterior chamber filled with the first viscoelastic substance with observing the moving of the second viscoelastic substance until the incision is sealed with the second viscoelastic substance, A schematic diagram of the above-described steps is shown in FIG. 1. FIG. 1 shows step (1), step (2) and step (3) in starting from the left.

By the present invention method 1, since the incision site is sealed with the second viscoelastic substance and a good depth of an anterior chamber is kept by the first viscoelastic substance, (with the proviso the an anterior chamber is kept by both of a different viscoelastic substance from the first viscoelastic substance and the first viscoelastic substance when the different viscoelastic substance is injected in the step (3)) a good operability and a superior protective effect for corneal endothelium are provided following ophthalmic surgery. In addition, any ophthalmologist can produce uniformly quality and stable operative procedures without depending on experience and skill level with ophthalmic surgery because of easy ways.

Furthermore, the present invention method 1 can be used for every ophthalmic surgery, particularly preferably for micro-incision cataract surgery.

<2> The Present Invention Method 2

The present invention method 2 is preferably used for a micro-incision ophthalmic surgery wherein the aqueous humor is discharged by anterior chamber paracentesis.

The present invention method 2 comprises at least, in the order mentioned, the steps of:

(1) discharging an aqueous humor by anterior chamber paracentesis;

(2) injecting a second viscoelastic substance into an area around a puncture wound in an anterior chamber through the puncture wound; and
(3) injecting a first viscoelastic substance having a lower surface tension than that of the second viscoelastic substance into an area of the anterior chamber which is distant from an area which has already been filled with the second viscoelastic substance in the anterior chamber through the puncture wound until the puncture wound is sealed with the already injected second viscoelastic substance.

Moreover the above-described anterior chamber paracentesis may be carried out not only in the usual manner with a needle but also in a manner with a tool other than a needle as long as aqueous humor can be appropriately eliminated from an anterior chamber. Therefore the puncture wound described above may be not only a puncture wound but also a small incision or a wound like puncture which is made by a tool other than a needle.

<2>-1 Viscoelastic Substance

Viscoelastic substances used for the present invention method 2, i.e. "a second viscoelastic substance" and "a first viscoelastic substance", are the same as in the present invention method 1 (<1>-1).

<2>-2 Specific Steps of the Present Invention Method 2

Feature of the present invention method 2 comprises at least the following three steps in a micro-incision ophthalmic surgery. The steps are
(1) discharging an aqueous humor by anterior chamber paracentesis;
(2) injecting a second viscoelastic substance into an area around a puncture wound in an anterior chamber through the puncture wound, and
(3) subsequently injecting a first viscoelastic substance having a lower surface tension than that of the second viscoelastic substance into an area of the anterior chamber which is distant from an area which has already been filled with the second viscoelastic substance through the puncture wound until the puncture wound is sealed with the already injected second viscoelastic substance.

The step (2) is a step of injecting a second viscoelastic substance through a puncture wound into an area around the puncture wound in an anterior chamber.

A second viscoelastic substance used herein is the same as "a second viscoelastic substance" which is previously described in the present invention method 1. The step (1) is a step for making puncture wound for discharging an aqueous humor. The step (2) is a step that in cases where an aqueous humor is discharged from an anterior chamber by an anterior chamber paracentesis in a micro-incision ophthalmic surgery, the second substance is injected through the puncture wound into the anterior chamber. An area into which the second viscoelastic substance should be injected is an area around the puncture wound in the anterior chamber. Therefore, it can be achieved by placing a tip of device such as an injector needle which is used for injecting the viscoelastic substance in a position which is capable that the second viscoelastic substance can be injected into the area around the puncture wound in the anterior chamber followed by injection of the second viscoelastic substance.

Injected volume of the second viscoelastic substance is necessary to be volume which is enough to seal the puncture wound with the second viscoelastic substance in the following step (3). In general, it is much less than the volume of the first viscoelastic substance which is injected in the following step (3). Actual volume may be determined appropriately by those skilled in the art depending on a size of an incision, a size of anterior chamber and a desired result of surgical of individual patients, and the like. In cases where it is a cataract surgery on adult, if a shape of cornea which is viewed from directly above is "circle", a volume which can be filled up to approximately 10 to 20% of an area of the circle may be represented as an example. Absolutely it is not limited thereto.

Needless to say, when the second viscoelastic substance is injected, aqueous humor in an anterior chamber may be discharged through the puncture wound depending on the injected volume of the second viscoelastic substance.

The step (3) is carried out after the step (2). It is a step of injecting a first viscoelastic substance having lower surface tension than that of the second viscoelastic substance used in the above step (2) through the puncture wound into a distant area in the anterior chamber from the filled area with the previously injected second viscoelastic substance until the puncture wound is sealed with the second viscoelastic substance.

The first viscoelastic substance used herein is the same as "a first viscoelastic substance" which is previously described in the present invention method 1. In the step (3), the first viscoelastic substance is injected into an anterior chamber through a puncture wound. An area into which the first viscoelastic substance is injected is a distant area from a filled area with the previously injected second viscoelastic substance. Needless to say, the area is not filled with the previously injected second viscoelastic substance.

Therefore, a tip of device such as an injector needle used for injecting the first viscoelastic substance is positioned in a position which is capable that the first viscoelastic substance can be injected into a distant area from the area which is filled with the previously injected second viscoelastic substance (i.e. the distant area unfilled with the second viscoelastic substance in the anterior chamber) followed by injection of the first viscoelastic substance. In this case, the first viscoelastic substance can be injected into the anterior chamber while the tip of device pierces the previously injected second viscoelastic substance.

Volume of injecting the first viscoelastic substance is necessary to be a volume which is enough to seal the puncture wound with the previously injected second viscoelastic substance.

Therefore, actual volume depends on volume of the previously injected second viscoelastic substance, a size of puncture wound, a size of anterior chamber of individual patients, and the like.

Figure 2:
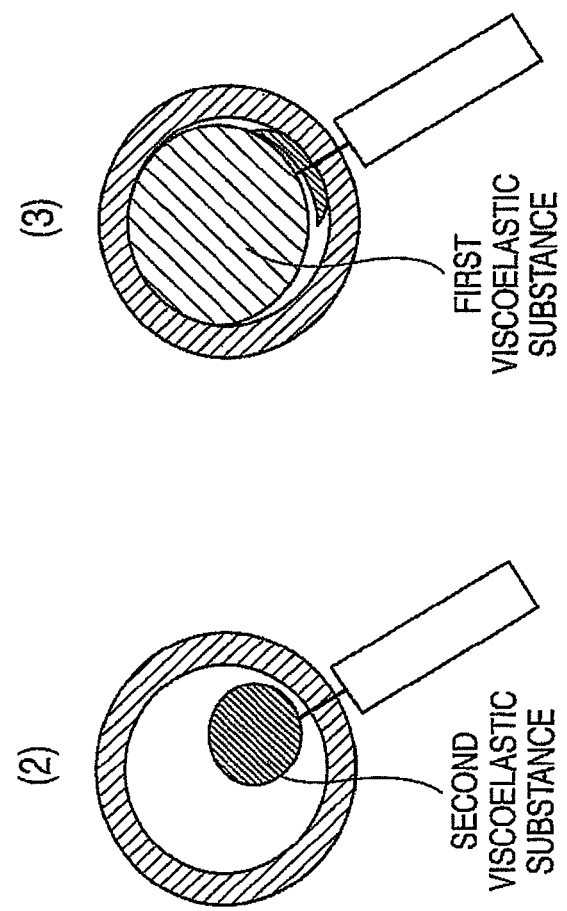
FIG. 2 is a schematic figure of steps (2) and (3) of the present invention method 2.

By injecting the first viscoelastic substance, aqueous humor is discharged through the puncture wound. Additionally, the previously injected second viscoelastic substance moves toward the puncture wound with the flow of aqueous humor to seal the puncture wound. Accordingly, the step (2) can be achieved by injecting the viscoelastic substance until the puncture wound can be sealed with the second viscoelastic substance with observing the moving of the second viscoelastic substance, A schematic diagram of the above-described steps (2) and (3) are shown in FIG. 2. FIG. 2 shows step (2) and step (3) in starting from the left. The present invention method 2 also can provide a good operability in the subsequently ophthalmic surgery since a good depth of anterior chamber in a cavity of anterior chamber is kept by the first viscoelastic substance and to seal a puncture wound by the second viscoelastic substance. Additionally, the present invention method 2 can provide a superior protective effect for corneal endothelium, too.

Furthermore, the present invention method 2 can be carried out with the uniformly quality and stable operative procedures by any ophthalmologists without considering their experience and skilled level of ophthalmic surgery since it is easy.

Additionally, the present invention method 2 can be also used for every micro-incision ophthalmic surgery, among them, particularly preferably for a micro-incision cataract surgery.

<3> The Present Invention Kit

The present invention kit is an ophthalmic surgery support kit which comprises at least the following components of (A) and (B) and is used for the present invention method.
(A) a first viscoelastic substance
(B) a second viscoelastic substance having higher surface tension than that of the first viscoelastic substance.

"A first viscoelastic substance" in above-mentioned (A) and "a second viscoelastic substance" in above-mentioned (B) is the same as in the present invention method 1 (the above-described <1>-1).

The kit can be provided as a kit comprising two individual containers. Namely, the above-described (A) and (B) respectively are filled to seal completely into separate containers and the containers can be provided for as a single set. Examples of a kind of container is not limited and the person skilled in the art can select a syringe, an ample, a vial and the like appropriately from various containers which can be filled with pharmaceuticals and completely-sealed followed by distribution and storage.

For example, in cases where the above-mentioned (A) and (B) are respectively filled in each individual syringe for injection, needless to say, it can be provide as a single set comprising such individual syringes.

Furthermore, it may be used an all-in-one syringe which is composed with more than two syringes or a syringe for injection which has several compartments inside. For example, an all-in-one syringe is made by arranging two syringes parallel to each another and binding them together as parallel, wherein each syringe is filled with the above-mentioned (A) and (B) respectively to be sealed completely and injection of the (A) or (B) can be carried out by selection. Another example is, a syringe having several compartments, wherein one compartment is filled with the above (A) and the other compartment is filled with the above (B) with sealing both compartments completely. By using the syringe having several compartments inside, injection of the (A) or (B) can be carried out by selection.

The present invention kit is an ophthalmic surgery support kit used in the present invention method. Therefore, the present invention kit can be used according to the above-described the present invention method. Specifically, in cases where the present invention kit is used in the present invention method 1, the above-mentioned (A) (a first viscoelastic substance) may be used in Step (1) and Step (3) and the above-mentioned (B) (a second viscoelastic substance) may be used in Step (2). And in cases where the present invention kit is used in the present invention method 2, the above-mentioned (B) (a second viscoelastic substance) may be used in Step (2) and the above-mentioned (A) (a first viscoelastic substance) may be used in Step (3).

The present invention kit can be used in any micro-incision ophthalmic surgery of the present invention method, among these particularly preferably in a micro-incision cataract surgery.

The present invention kit is only necessary to comprises at least the above-mentioned (A) and (B) as components. Needless to say, the present invention kit may comprises another components. For example, in cases where the present invention kit is provided as a form of a syringe for injection, various attachment members which are connected to the syringe for injection in use can be further comprised. Needless to say, an explanatory leaflet about the present invention method 1 and/or 2 and the like can be included in the present invention kit.

In cases where viscoelastic substances used in all steps in the present invention method are an aqueous solution containing sugar chains, wherein a kind of sugar chains and a concentration of the sugar chain in the aqueous solution used in all steps is the same, the term of "a surface tension" in this description may be replaced with the term of "a weight-average molecular weight of the sugar chain in the aqueous solution". Meanwhile for the present invention kit, the above-mentioned viscoelastic substances mean components (A) and (B).

For example, when both of the components (A) and (B) of the present invention kit are an aqueous solution comprising hyaluronic acids or salts thereof at a concentration of 1% (w/v), the component (B) which should be used can be replaced with "a second viscoelastic substance which is an aqueous solution comprising hyaluronic acids or salts thereof, in which hyaluronic acid or a salt thereof has a higher weight-average molecular weight than that in the first viscoelastic substance of the component (A)". Accordingly in this case, the second viscoelastic substance of the component (B) can be used an aqueous solution comprising hyaluronic acids or salts thereof, in which hyaluronic acid or a salt thereof has a higher weight-average molecular weight than that in the first viscoelastic substance of the component (A). It is also similar to the present invention method 1 and 2.

A viscoelastic substance can be a composition of several materials. An act of viscoelastic substance can be suitably controlled in various cases by using such combinations. For example, in cases where a mixture of aqueous solution containing hyaluronic acid or a salt thereof at a concentration of about 1% (w/v), in which hyaluronic acid or a salt thereof has a weight-average molecular weight in the range of from 600,000 to 1,200,000, (for example, OPEGAN®) and an aqueous solution containing hyaluronic acid or a salt thereof at a concentration of about 1% (w/v), in which hyaluronic acid or a salt thereof has a weight-average molecular weight in the range of from 1,900,000 to 3,900,000, (for example, OPEGAN-Hi®) is used, the more the former is used, the higher retention on the inside of cornea (higher protective effects of corneal endothelium) of the mixture is obtained. On the other hand, the more the latter is used, keeping the cavity of anterior chamber is better and suction of the viscoelastic substance as a clot can be carried out with better efficacy.

Considering such properties, a composition which is prepared appropriately depending on each case of diseases or conditions can be used in every step of the present invention method and it can be used also in micro-incision ophthalmic surgery other than the present invention method.

The present invention kit may contain containers which are filled with the above-mentioned (A) and (B) respectively and hermetically-sealed and further a container for mixing the (A) and (B).

Needless to say, the container for mixing may be an injection syringe. As described above, for example, it may be an all-in-one syringe which is composed with injection syringes filled with the (A) and (B) respectively and her-metically-sealed as well as further a injection syringe for mixing if necessary. Another example is a syringe for injection having a compartment for mixing inside.

The present invention method (Dual Visco Sealed-Up Technique) is extremely useful. The present invention method provides good operation performance caused by keeping depth of the anterior chamber and superior protective effects for corneal endothelium. According to the present invention method, any ophthalmologist can carry out ophthalmic surgeries such as cataract surgery with easy and stable operative procedures and the uniform quality without depending on their skill and experience level with ophthalmic surgery. The present invention method can also speed-up of surgery. In the other words, the present invention method can produce good postoperative results and make such results universal. Even an ophthalmologist who has little experience with ophthalmic surgery can show equal postoperative results as an ophthalmologist who has lots of experience with ophthalmic surgery. Finally the present invention method contributes to eliminating health disparities, improving healthcare and bringing uniform quality.

Furthermore, the present invention method is very useful in view of the following points. Since elimination of the injected viscoelastic substance is easy and risks of postoperative bacterial endophthalmitis are decreased, the postoperative elevation of intraocular pressure in cataract disorder and the like is prevented (i.e. the side effects can be decreased). Therefore, according to the present invention method, the aggravation of symptoms caused by the surgery can be prevented.

Moreover the present invention method is very useful since it can be applied for cataract surgery for which the conventional soft shell technique can not be used.

Additionally, the present invention method does not need to re-inject a viscoelastic substance because of little leakage amount of injected viscoelastic substance during a surgery. Therefore, it can cut-down usage amount of viscoelastic substance. Namely, in view of the economic benefits, the present invention method is also very useful.

The present invention method extremely contributes not only expanding the range of case which is capable of treating by a surgery but also improving quality of life on patients by relieving their burdens and anxieties about a surgery.

Additionally, needless to say, the present invention kit is very useful to make the present invention method speedy.

The present invention will be described in detail by referring to Examples. However, the Examples are not intended to limit the technical scope of the present invention.

Examples

<1> The Present Invention Method 1

In the present invention method 1, "OPEGAN®" (produced by SEIKAGAKU CORPORATION) was used as a first viscoelastic substance of step (1); "OPEGAN Hi®" (produced by SEIKAGAKU CORPORATION) was used as a second viscoelastic substance of step (2); and the above-mentioned OPEGAN® is used as a third viscoelastic substance of step (3) "OPEGAN®" used herein contains sodium hyaluronate having a weight-average molecular weight of 900,000 and "OPEGAN Hi®" used herein contains sodium hyaluronate having a weight-average molecular weight of 2,400,000.

The present invention method 1 was performed on pigs (total 20 eyes). As a result, a good depth of an anterior chamber was kept and a good operability of the subsequent ophthalmic surgery procedures are provided. Therefore, the surgery which provided a stable and good uniform quality could be performed quite easily as well as in short time.

Furthermore, repetitive injection of the viscoelastic substance is not needed because of less leakage of the viscoelastic substance during the surgical procedures. Additionally, after the surgical procedures, the viscoelastic substance could be easily and fully eliminated and the prognosis was excellent without particular side effects such as elevation of intraocular pressure.

The ophthalmic surgery by the present invention method 1 was performed on 300 cataract patients. All cases showed keeping a good depth of an anterior chamber and providing a good operability of the subsequently ophthalmic surgery procedures. Therefore, the surgery which provided a stable and good uniform quality could be performed quite easily as well as in short time. Additionally, after the surgical procedures, the viscoelastic substance could be eliminated easily as well as fully and the prognosis was excellent without particular side effects such as elevation of intraocular pressure.

The Present Invention Method 2

In the present invention method 2, the above-mentioned "OP EGAN-Hi®" was used as a second viscoelastic substance in step (2) and the above-mentioned "OPEGAN®" was used as a first viscoelastic substance in step (3).

The present invention method 2 was performed on pigs (total 10 eyes). As a result, a good depth of an anterior chamber was kept and a good operability of the subsequently ophthalmic surgery procedures was provided. Therefore, the surgery which provided a stable and good uniform quality could be performed quite easily as well as in short time. Furthermore, it did not need to repeat injection of the viscoelastic substance because of little leak of the viscoelastic substance during the surgical procedures. Additionally, after the surgical procedures, the viscoelastic substance could be eliminated easily as well as fully and the prognosis was excellent without particular side effects such as elevation of intraocular pressure.

The ophthalmic surgery by the present invention method 2 was performed on 80 cataract patients. All cases kept a good depth of an anterior chamber and provided good operability for the subsequent ophthalmic surgery procedures. Therefore, the surgery provided a stable and good uniform quality, and could be performed quite easily as well as in less time. Additionally, after the surgical procedures, the viscoelastic substance could be eliminated easily as well as fully and the prognosis was excellent without particular side effects such as elevation of intraocular pressure.

<The Present Invention Kit>

The present invention kit comprising the following components was made.

(1) A phosphate-buffered saline containing sodium hyaluronate having a weight-average molecular weight of 900,000 at a concentration of 1% (w/v) (i.e. an injector syringe filled with an aqueous solution containing sodium hyaluronate equivalent for OPEGAN®.)

(2) A phosphate-buffered saline containing sodium hyaluronate having a weight-average molecular weight of 2,400,000 at a concentration of 1% (w/v) (i.e. an injector syringe filled with an aqueous solution containing sodium hyaluronate equivalent for OPEGAN-Hi®.)

Although the present invention has been described in detail with reference to specific examples in the foregoing, it is apparent to person skilled in the art that it is possible to add various alterations and modifications insofar as the alterations and the modifications do not deviate from the sprit and scope of the present invention.

This patent application is based on U.S. provisional Patent Application No. 61/024,589 filed on Jan. 30, 2008, and the contents thereof are incorporated herein by reference.

I claim:

1. A method of micro-incision ophthalmic surgery, comprising, in the order mentioned, the steps of:
   (1) injecting a first viscoelastic substance through an incision site which is to the side of the cornea filling a part of the anterior chamber opposite the incision site with discharging aqueous humor and without coating the anterior capsule:
   (2) injecting a second viscoelastic substance having higher surface tension than that of the first viscoelastic substance through the incision site into a part of the anterior chamber at the same side as the incision site and such that the second substance contacts the incision site: and
   (3) injecting a third viscoelastic substance having lower surface tension than that of the second viscoelastic substance through the incision site into the part of the anterior chamber which is filled with the first viscoelastic substance until the incision site is sealed with the already injected second viscoelastic substance.

2. The method according to claim 1, wherein the viscoelastic substances are aqueous solutions containing a sugar chain.

3. The method according to claim 2, wherein the sugar chain is a glycosaminoglycan.

4. The method according to claim 3, wherein the glycosaminoglycan is hyaluronic acid or a salt thereof.

5. The method according to claim 4, wherein a weight-average molecular weight of the hyaluronic acid or a salt thereof is in the range of from 600,000 to 4,000,000.

6. The method according to claim 1, wherein the first viscoelastic substance described in above (1) and the third viscoelastic substance described in above (3) are the same viscoelastic substance.

7. The method according to claim 1 or 6, wherein the first viscoelastic substance is an aqueous solution containing hyaluronic acid or a salt thereof, in which the hyaluronic acid of the salt thereof has a weight-average molecular weight in the range of from 600,000 to 1,200,000.

8. The method according to claim 1 or 6, wherein the second viscoelastic substance is an aqueous solution containing hyaluronic acid or a salt thereof, in which the hyaluronic acid or the salt thereof has a weight-average molecular weight in the range of from 1,500,000 to 4,000,000.

9. The method according to claim 8, wherein the hyaluronic acid or the salt thereof has a weight-average molecular weight in the range of from 1,900,000 to 3,900,000.

10. The method according to claim 4, wherein the concentration of the aqueous solution containing the hyaluronic acid or the salt thereof is about 1% (w/v).

11. A method of micro-incision ophthalmic surgery, comprising, in the order mentioned, the steps of:
    (1) injecting a first viscoelastic substance, which is an aqueous solution containing hyaluronic acid or a salt thereof, wherein a concentration of hyaluronic acid or a salt thereof in the aqueous solution is about 1% (w/v) in which hyaluronic acid or a salt thereof has a weight-average molecular weight in the range of from 600,000 to 1,200,000, through an incision site which is to the side of the cornea filling a part of the anterior chamber opposite the incision site with discharging aqueous humor and without coating the anterior capsule:
    (2) injecting a second viscoelastic substance, which is an aqueous solution containing hyaluronic acid or a salt thereof, wherein a concentration of hyaluronic acid or a salt thereof in the aqueous solution is about 1% (w/v) in which hyaluronic acid or a salt thereof has a weight-average molecular weight in the range of from 1,900,000 to 3,900,000 and which has higher surface tension than that of the first viscoelastic substance, through the incision site into a part of the anterior chamber at the same side as the incision site and such that the second substance contacts the incision site; and
    (3) injecting a third viscoelastic substance, which is an aqueous solution containing hyaluronic acid or a salt thereof, wherein a concentration of hyaluronic acid or a salt thereof in the aqueous solution is about 1% (w/v) in which hyaluronic acid or a salt thereof has a weight-average molecular weight in the range of from 600,000 to 1,200,000 and which has lower surface tension than that of the second viscoelastic substance, through the incision site into the part of the anterior chamber which is filled with the first viscoelastic substance until the incision site is sealed with the already injected second viscoelastic substance.

12. The method of claim 4, wherein the salt is a sodium salt, a lithium salt, a potassium salt, an ammonium salt, diethanolamine salts, cyclohyxylamine salts or an amino acid salt.

* * * * *